United States Patent [19]
Fleming et al.

[11] Patent Number: 5,893,269
[45] Date of Patent: Apr. 13, 1999

[54] CRYSTAL FREEZING APPARATUS

[75] Inventors: Patrick J. Fleming, Guilford; Gerald E. Johnson, Bethany, both of Conn.; Alan M. Friedman, West Lafayette, Ind.

[73] Assignee: Yale University, New Haven, Conn.

[21] Appl. No.: 09/065,784

[22] Filed: Apr. 23, 1998

Related U.S. Application Data

[60] Provisional application No. 60/050,948, Jun. 12, 1997.
[51] Int. Cl.[6] .............................. F25B 19/00; F25D 17/02
[52] U.S. Cl. ........................................... 62/51.1; 62/373
[58] Field of Search ............................ 62/51.1, 78, 373, 62/374, 336, 340, 601

[56] References Cited

U.S. PATENT DOCUMENTS

| | | | |
|---|---|---|---|
| 4,551,992 | 11/1985 | Sitte et al. | 62/51.1 |
| 4,563,883 | 1/1986 | Sitte | 62/51.1 |
| 4,723,420 | 2/1988 | Sitte | 62/51.1 |
| 4,967,571 | 11/1990 | Sporri | 62/373 |

*Primary Examiner*—William Doerrler
*Attorney, Agent, or Firm*—Ohlandt, Greeley, Ruggiero & Perle

[57] ABSTRACT

A crystal freezing apparatus in accordance with the invention includes a first chamber for receiving a macromolecular structure and a second chamber which includes a cryogenic liquid holder. Gas inlets are provided for introducing a defined gas, such as Xenon at an elevated pressure, into both chambers. Introduction of the defined gas into the first chamber, enables atoms of the defined gas to enter void spaces in or onto the surface of the macromolecular structure while it is held in the first chamber. A valve structure is provided to connect the first and second chambers. A push rod assembly enables movement of the macromolecular structure from the first chamber to the second chamber, via the valve structure, all while under the influence of the defined gas. Once the macromolecular structure enters the second chamber, it is immersed into a cryogenic liquid so as to freeze the macromolecular structure with its included atoms of the defined gas.

9 Claims, 1 Drawing Sheet

CRYSTAL FREEZING APPARATUS

This invention claims priority from Provisional Patent Application, Serial No. 60/050,948, filed Jun. 12, 1997.

The United States Government has rights in this invention as a result of support of the development thereof under Public Health Service Grant P01 GM 22778.

FIELD OF THE INVENTION

This invention relates to apparatus for freezing macromolecules for the purpose of X-ray diffraction analysis and, more particularly, to an apparatus for freezing such macromolecular structures in a defined atmosphere to enable a determination of the crystalline structure thereof.

BACKGROUND OF THE INVENTION

The determination of protein, DNA and RNA crystal structure using X-ray diffraction methods is an important and expanding area of biology and biomedical science. Many laboratories around the world are involved in X-ray crystallography. The scientific effort in this area is increasing exponentially and as a result of the human genome project, is expected to even further accelerate.

A critical and usually rate-limiting step in the determination of macromolecular structures by X-ray crystallography is the preparation of heavy-atom derivatives of the crystal. Typical derivatives use mercury or lead-based chemicals which bind to the macromolecular crystal. The scientist, however, may need to screen hundreds of such chemicals before finding a successful derivative.

Xenon is a noble gas which binds to specific sites in a macromolecule. Recent experiments have shown that Xenon-protein complexes can serve as heavy atom derivatives in approximately 50% of all cases studied. The Xenon-protein derivative is obtained by equilibrating the protein crystal under a Xenon gas atmosphere, at a relatively low pressure. Unless the pressure is maintained or the complex is frozen to a very low temperature, the Xenon is released from the complex.

Coincidentally, the use of very low temperatures during the collection of X-ray diffraction data is advantageous because it prevents radiation damage to the crystal and affords a more stable crystal, resulting in better data. Collection of X-ray diffraction data at cryogenic temperatures has become the default method for macromolecular crystallography.

Accordingly, there is a need for apparatus which enables incorporation of Xenon atoms into macromolecular structures to enable improved X-ray crystallography thereof. Further, such apparatus must be constructed so as to maintain the macromolecular structure under the influence of the Xenon atmosphere, both during equilibration and during freezing.

SUMMARY OF THE INVENTION

A crystal freezing apparatus in accordance with the invention includes a first chamber for receiving a macromolecular structure and a second chamber which includes a cryogenic liquid holder. Gas inlets are provided for introducing a defined gas, such as Xenon at an elevated pressure, into both chambers. Introduction of the defined gas into the first chamber, enables atoms of the defined gas to enter void spaces in the macromolecular structure while it is held in the first chamber. A valve structure is provided to connect the first and second chambers. A push rod assembly enables movement of the macromolecular structure from the first chamber to the second chamber, via the valve structure, all while under the influence of the defined gas. Once the macromolecular structure enters the second chamber, it is immersed into a cryogenic liquid so as to freeze the macromolecular structure with its included atoms of the defined gas.

BRIEF DESCRIPTION OF THE DRAWINGS

The FIGURE is a schematic view of a crystal freezing apparatus in accordance with the invention.

DETAILED DESCRIPTION OF THE INVENTION

Figure 1:
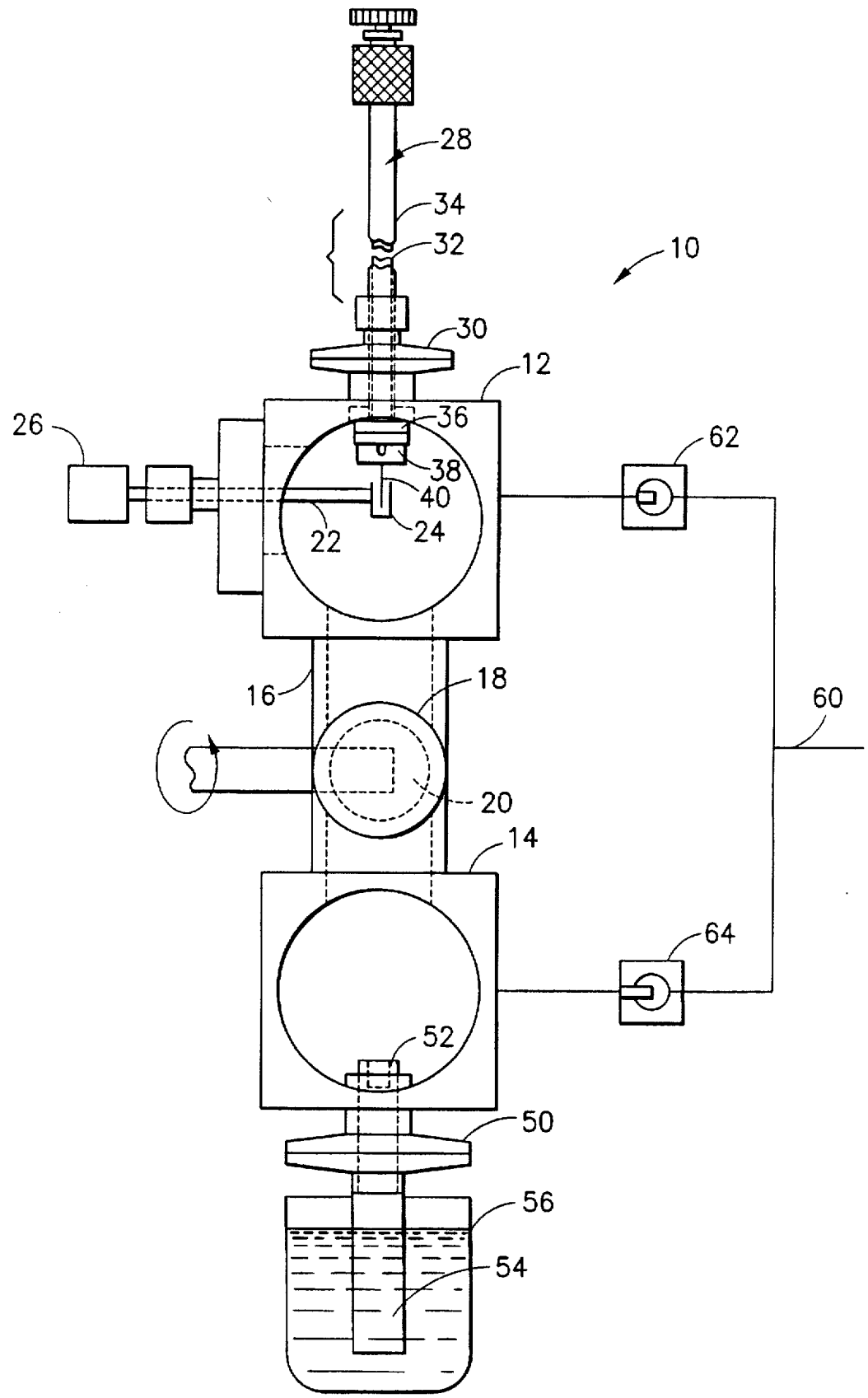

Crystal freezing apparatus 10 comprises an upper chamber 12 and lower chamber 14. A ball valve structure 16 connects upper chamber 12 to lower chamber 14. Ball valve 18 includes an orifice 20 which, when rotated 90°, enables communication between upper chamber 12 and lower chamber 14.

Upper chamber 12 includes a sliding arm 22 which holds a cup 24 for mother liquor or a cryoprotectant (e.g., a pH buffered salt solution or a solution containing polyhydroxy compounds). Cup 24 may be positioned along the center line of upper chamber 12 or moved to the edge of the chamber by the action of sliding arm 22, as actuated by knob 26. A push rod assembly 28 enters upper chamber 12 via a flange seal 30. Push rod assembly 28 comprises an inner rod 32 and an outer tube 34. At the distal end of outer tube 34, is a magnet 36 which holds a base 38, from which a sample pin 40 extends. A macromolecular sample may be held by sample pin 40, in the known manner.

Outer tube 34 slides up and down in flange seal 30 to enable a repositioning of sample pin 40. Rod 32, when depressed downwardly, is adapted to push base 38 and cause its release from the attraction of magnet 36.

Lower chamber 14 includes a flange seal 50 which accepts a vial holder 52 into which a vial filled with a cryogenic liquid, such as propane or freon. A metal rod 54 of thermally conductive metal extends downwardly from flange seal 50 and is immersed in a liquid nitrogen bath held by container 56. Rod 54 is preferably of copper or another highly thermally conductive metal which maintains vial holder 52 at a cryogenic temperature.

A source of a defined gas 60 is provided for both upper chamber 12 and lower chamber 14 and enables, through control valves 62 and 64, a pressurization of both chambers with the defined gas to a desired level. A preferred defined gas is Xenon, however other defined gases such as krypton or volatile organic compounds will work in a similar manner. It is preferred that all fittings be sealed to maintain pressures of about 200 psi or higher. Control valves 62 and 64 enable a venting of the defined gas from either or both chambers 12 and 14.

The operation of crystal freezing apparatus 10 is hereafter described. Initially, a macromolecular sample which is to be subjected to X-ray crystallography, is mounted in a filament loop on the distal end of sample pin 40. Sample pin 40 and base 38 are then attached to magnet 36, within upper chamber 12, and push rod assembly 28 is clamped securely. The mother liquor/cryoprotectant cup 24 is moved into the center of upper chamber 12 and outer tube 34 is actuated downwardly so as to place the macromolecular sample inside cup 24. The macromolecular sample may either be submerged in the mother liquor/cryoprotectant or held just above its meniscus, to prevent a drying out of the sample. If it is submerged, special loops are required to prevent loss of the sample.

At such time, the defined gas is introduced into upper chamber 12 to a desired pressure (e.g., 150–1000 psi). The system is then allowed to equilibrate for a period of time, e.g., 10 minutes. During the equilibration time, copper rod 54 is submerged into a liquid nitrogen bath within container 56, causing vial holder 52 to reach cryogenic temperatures. A vial of solid, frozen propane is placed in vial holder 52 and, when just melted, the entire structure, comprising vial holder 52, connected copper rod 54 and container 56, is raised to insert vial holder 52 (and its supported vial of propane) into lower chamber 14. The propane is thus maintained at approximately −180° Centigrade.

After the above-described equilibration time, lower chamber 14 is pressurized with xenon gas to the same pressure as is present in upper chamber 12. Then, ball valve 18 is rotated to enable communication between upper chamber 12 and lower chamber 14. Sample pin 40, including the macromolecular sample, is now raised out of cup 24 and, by withdrawal of knob 26, cup 24 is moved away from sample pin 40. Next, tube 34 is depressed downwardly to move sample pin 40 through opening 20 in ball valve 18 and into lower chamber 14.

When the macromolecular sample is just above the vial of propane, rod 32 is pushed downwardly causing a release of sample pin 40 and the included macromolecular sample into the propane, thereby causing a flash freezing of the macromolecular sample into its crystalline form.

Thereafter, the system is vented and vial holder 52 and connected copper rod 54 are unclamped and removed from the apparatus. The vial containing sample pin 40 with the crystallized sample is retrieved and placed in liquid nitrogen for transport. Crystal freezing apparatus thereby allows the freezing of macromolecular crystals under defined conditions of gas and pressure and assures that atoms of the gas, which have equilibrated in the sample, remain equilibrated during the freezing action.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

We claim:

1. A crystal freezing apparatus, comprising:

a first chamber for receiving a macromolecular structure;

a second chamber including means for holding a cryogenic liquid;

means for introducing a defined gas at an elevated pressure into said first chamber and said second chamber, said defined gas in said first chamber enabling atoms of said defined gas to infiltrate said macromolecular structure;

valve means for connecting said first chamber to said second chamber; and means for moving said macromolecular structure from said first chamber to said second chamber, via said valve means, to cause an immersion of said macromolecular structure into said cryogenic liquid so as to freeze said macromolecular structure after atoms of said defined gas have infiltrated said macromolecular structure.

2. The crystal freezing apparatus as recited in claim 1, wherein said means for moving said macromolecular structure includes push rod means mounted in said first chamber for holding said macromolecular structure, said push rod means actuatable to move said macromolecular structure through said valve means and into said second chamber.

3. The crystal freezing apparatus as recited in claim 2, wherein said first chamber further includes a cup for containing a cryoprotectant, said push rod means oriented, upon actuation, to bring said macromolecular structure into contact with said cryoprotectant during exposure to said atoms of said defined gas.

4. The crystal freezing apparatus as recited in claim 1, wherein said second chamber further includes a cup for containing said cryogenic liquid, said cup thermally coupled to a cryogenic refrigerant.

5. The crystal freezing apparatus as recited in claim 4, wherein said cup for containing said cryogenic liquid is thermally coupled to said cryogenic refrigerant via a thermally conductive support.

6. The crystal freezing apparatus as recited in claim 1, wherein said defined gas is maintained at an elevated pressure in said second chamber during the freezing of said macromolecular structure.

7. The crystal freezing apparatus as recited in claim 1, wherein said cryogenic liquid is propane or freon.

8. The crystal freezing apparatus as recited in claim 1, wherein said defined gas is a noble gas or a volatile organic compound.

9. The crystal freezing apparatus as recited in claim 1, further comprising:

means for opening said valve means to enable passage of said push rod means after atoms of said defined gas have become equilibrated in said macromolecular structure and for closing said valve means prior to equilibration, said push rod means including means for enabling release of said macromolecular structure into said cryogenic liquid.

* * * * *